United States Patent
Utpal et al.

(10) Patent No.: US 7,611,853 B2
(45) Date of Patent: Nov. 3, 2009

(54) ASSAY TO SCREEN FOR ANTI-MALARIALS

(75) Inventors: Tatu Utpal, Bangalore (IN); Pavithra Soundara Raghavan, Bangalore (IN); Banumathy Gowrishankar, Bangalore (IN)

(73) Assignee: Indian Institute of Science, Bangalore, IN (US)

( * ) Notice: Subject to any disclaimer, the term of this patent is extended or adjusted under 35 U.S.C. 154(b) by 324 days.

(21) Appl. No.: 10/539,728

(22) PCT Filed: Dec. 1, 2003

(86) PCT No.: PCT/IN03/00374

§ 371 (c)(1),
(2), (4) Date: Apr. 5, 2006

(87) PCT Pub. No.: WO2004/057327

PCT Pub. Date: Jul. 8, 2004

(65) Prior Publication Data

US 2006/0183167 A1    Aug. 17, 2006

(30) Foreign Application Priority Data

Dec. 20, 2002    (IN) ......................... 965/MAS/2002

(51) Int. Cl.
*G01N 33/543*    (2006.01)
*G01N 33/569*    (2006.01)
*C07K 14/445*    (2006.01)

(52) U.S. Cl. .................. 435/7.22; 435/7.5; 435/7.8; 435/7.93; 435/7.95; 435/287.9; 435/947; 436/503; 436/518; 436/524; 436/527; 436/86; 436/172; 436/175; 436/177; 530/822; 530/350

(58) Field of Classification Search ................. 435/7.22, 435/7.5, 7.8, 7.93, 7.95, 287.9, 947; 436/503, 436/518, 524, 527, 86, 172, 175, 177; 530/350
See application file for complete search history.

(56) References Cited

FOREIGN PATENT DOCUMENTS

WO    03/050295    *    6/2003

OTHER PUBLICATIONS

Jendoubi et al., 1985. Characterization of one polypeptide antigen potentially related to protective immunity against the blood infection by *Plasmodium falciparum* in the squirrel monkey. J. Immunology 134: 1941-1954.*

Banumathy et al., 2002. Host charperones are recruited in membrane-bound complexes by *Plasmodium falciparum*. J. Biol. Chem. 277: 3902-3912.*

Bonnefoy et al., 1994. Molecular characterization of the heat shock protein 90 gene of the human malaria parasite *Plasmodium falciparum*. Mol. Biochem. Parasitol. 67: 157-170.*

Chiosis et al., 2001. A small molecule designed to bind to the adenine nucleotide pocket of Hsp90 causes Her2 degradation and the growth arrest and differentiation of breast cancer cells. Chem. & Biol. 8: 289-299.*

DeBoer et al., 1970. Geldanamycin, a new antibiotic. J. Antibiotics 23: 442-447.*

* cited by examiner

*Primary Examiner*—Mark L Shibuya
*Assistant Examiner*—James L Grun
(74) *Attorney, Agent, or Firm*—Harness, Dickey & Pierce, PLC

(57) ABSTRACT

Malarial parasite *Plasmodium falciparum* is responsible for the most severe form of malaria in humans, causing about 2 million deaths every year. Lack of effective vaccines and emergence of drug-resistant strains necessitate the need of novel drug targets to treat the disease. The present invention describes a novel assay method of identifying candidate compounds as anti-malarials based on the property of binding to plasmodial parasite 90 kDa heat shock protein.

9 Claims, 1 Drawing Sheet

ASSAY TO SCREEN FOR ANTI-MALARIALS

Figure 1A:
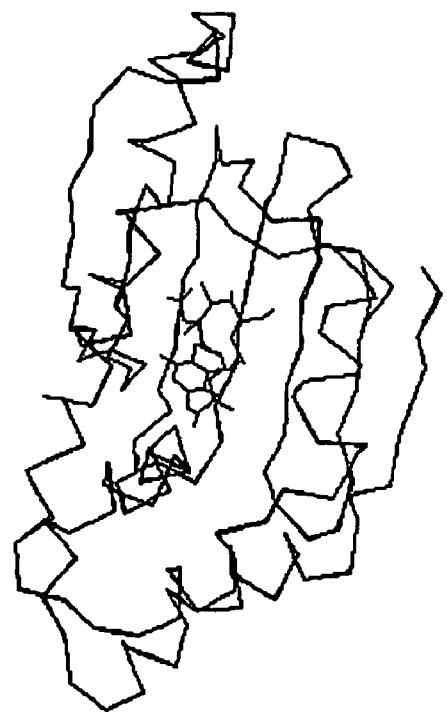

This invention relates to a novel assay to screen for anti-malarial drugs using plasmodial heat shock protein 90 as target.

PRIOR ART

Hsp90 is an abundant protein in eukaryotes comprising of 1-2% of total cellular proteins. It is indispensable for viability of yeast (1). In addition, Hsp90 is also shown to be essential for growth and development in fruit flies (2) and plants (3). Hsp90 in concert with Hsp70 and other co-chaperones, aids in the folding of certain subset of newly synthesized proteins and helps them to attain their mature, functional conformation. It associates with a variety of substrates in the eukaryotic cytosol like transcription factors (steroid receptors, aryl hydrocarbon receptor, heat shock factor, mutant p53, etc.), kinases ($pp60^{v-src}$, Raf-1, eIF-2α kinase, etc.), cytoskeletal proteins (actin and tubulin), telomerase, and proteosomes, thus participating in several important cellular functions like regulation of gene expression, signal transduction, cell proliferation and protein degradation (4, 5).

This multi-functional protein has also been shown to take part in protein targeting by associating with different co-chaperones. For instance, it utilizes the co-chaperone $p50^{cdc37}$ to transport kinases to plasma membrane and it uses FKBPs and p23 to translocate steroid receptors from cytosol to nucleus.

Hsp90, in combination with Hsp70 and Hop (Hsp70-Hsp90 organizing protein) forms multi-chaperone machinery in the eukaryotic cytosol (6). This pre-formed complex forms a part of "foldosome", which helps in the folding and assembly of client proteins. During stress, it prevents misfolding and non-specific aggregation of proteins. It is also involved in the folding of tumor suppressor protein, p53.

Hsp90 is found in elevated levels in several tumor cell lines. In tumor cells, Hsp90 stabilizes oncogenic protein kinases, mutated p53, etc. and thus takes part in tumor cell proliferation (7). Inhibiting Hsp90 function in tumor cells would therefore cause reversion to normal phenotype.

Ansamycin antibiotics, Geldanamycin (GA) and Herbimycin A (HA) were isolated from the fungus, *Streptomyces hygroscopicus*. The ansa ring of GA and HA resembles the adenine base of ATP and benzoquinone moiety is analogous to the ribose and phosphate group of ATP. Hence they compete with ATP in binding to ATP-binding domain of Hsp90 (8). GA is known to interfere with Hsp90 function by associating with ATP-binding pocket. When cell extracts were passed through GA-immoblized column, Hsp90 was the only protein from cell lysates that specifically bound to the column (9,10).

During its asexual life cycle in human erythrocytes, the malarial parasite progresses through three growth phases (11). The early form following invasion, called the ring stage, is the phase of establishment in the erythrocyte. Trophozoite stage is the metabolically most active, biosynthetic phase while the schizont stage represents the phase of nuclear division before release of merozoites from the erythrocyte. Heat shock proteins of the class Hsp60, Hsp70 and Hsp90 are known to be expressed by the parasite during the intra-erythrocytic stages in the vertebrate host (12,13,14). While these heat shock proteins share significant homologies with their mammalian counterparts, there is very limited information available about their functional roles in parasite development.

Hsp90 of *Plasmodium falciparum* (PfHsp90) is encoded by a single copy gene located in chromosome 7. The gene has a single intron of 800 bp and the encoded protein product has 745 amino acids with a molecular weight of 86 kDa (15). PfHsp90 sequence is highly conserved across various species. It shows 59% identity and 69% similarity to mammalian Hsp90. Very limited information is available regarding the functional role of PfHsp90 (16,17).

OBJECTIVE OF INVENTION

While it was well known that plasmodial Heat shock proteins of the class Hsp60, Hsp70 and Hsp90 are known to be expressed by the parasite during the intra-erythrocytic stages in the vertebrate host and that these heat shock proteins share significant homologies with their mammalian counterparts, there is very limited information available about their functional roles in parasite development. The objective of the invention was to determine whether these heat shock proteins are functionally important in the growth of parasites in vivo and in vitro using HSP90 as a model and develop suitable screening assays that will be useful to test chemical library of compounds and select novel anti-malarial agents.

SUMMARY OF INVENTION

The sequence alignment of *Plasmodium falciparum* HSP90 with human HSP90 (α and β) and its homologue Grp94 show that N-terminal domain of PfHsp90 shares 69% identity with human Hsp90. Sequence comparison with human Hsp90 reveals that this domain has an ATP/Geldanamycin binding site. The GXXGXG motif in this domain essential for ATP-binding is present in PfHsp90 also. The residues, which make contact with GA in mammalian Hsp90, are also conserved in PfHsp90. Both Geldanamycin and Herbimycin A kill the malarial parasite at the stage of early trophozoite development thereby showing that compounds binding to the geldanamycin binding site can be potential anti-malarial agents. It has been shown in in vitro assays that geldanamycin binds to *Plasmodium falciparum* HSP90 and such binding can be quantified using suitable immunochemical or radiochemical or non-radioactive assays. It has therefore been possible to describe in the assays wherein any suitably immobilized compound can be tested for the potential to bind to *Plasmodium* HSP90; the specific anti-malarial effect of a compound that binds to *Plasmodium* HSP90 can then be tested using known methods. Such assays can be further developed into high throughput assays using the currently known technologies enabling screening of compound libraries as exemplified by the BIAcore assay.

DETAILED DESCRIPTION OF THE INVENTION

A prototype assay is described below:

1.0: Covalent immobilization of the test compound on suitable matrices such as Sepharose or BIAcore CM5 sensor chips by known methods.

2.0: Preparation of Saponin-freed Plasmodial trophozoite lysate. *P. falciparum* infected erythrocytes in the trophozoite stage were treated with a final concentration of 0.075% saponin in PBS (10 mM sodium phosphate (pH 7.4), 137 mM NaCl, 2.7 mM KCl.) and centrifuged at 4,500 rpm for 4 min. Parasites are in the pellet fraction and are then washed twice in PBS and lysed in TNESV buffer (50 mM Tris-HCl, (pH 7.5), 1% NP40, 2 mM EDTA, 100 mM NaCl, 1 mM orthovanadate).

3.0: Reacting the trophozoite lysate with the covalently immobilized test compound.

4.0: Detection of the compound bound *Plasmodium falciparum* 90 kDa heat shock protein. This can be performed either by western blotting using polyclonal antibodies to PfHsp90 or by use of radiolabeled trophozoite protein extracts and subsequent detection by phosphorimager analysis as described for analysis of GA binding in examples 3.1 to 3.4. All compounds showing more than 10% of total binding to PfHsp90 were used for further screening.

Known Covalent Immobilization methods are:
1. Photochemical coupling.
2. Covalent immobilization of biomolecules using beads coated with carboxyl groups (e.g., LiquiChip Carboxy Beads, Qiagen) using carbodiimide chemistry. In this process, beads are washed and incubated with an activator (typically EDC/NHS), washed again, the capture molecule is added and incubated, and the beads washed again.
3. Using immobilized PCR primers
4. Spatially controlled covalent immobilization of Biomolecules on silicon surfaces.

In addition, a non-radioactive assay for screening test compound and related compounds using SPR analysis with a BIAcore 2000™ (Amersham Biosciences) biosensor system may also be used based on technical details provided for GA binding in example 3.4. Briefly, test compound is covalently immobilized on the research CM5 sensor chips at a concentration of 20 mM in 8% DMSO using the amine coupling kit (1-ethyl-3-(dimethylaminopropyl) carbodiimide), (N-hydroxysuccinimide) provided by the manufacturer. For compounds of unknown structure, derivatization is done with biotin using photobiotin acetate (22) followed by BIAcore analysis using the BIAcore SA chip that carries a streptavidin surface. All measurements are carried out with TNESV buffer (50 mM Tris-HCl, (pH 7.5), 1% NP40, 2 mM EDTA, 100 mM NaCl, 1 mM orthovanadate). The surface regenerated by a 50 s pulse of 0.5% SDS flowing at 10 µL/min. For binding analysis, saponin released trophozoites of *P. falciparum* are lysed in an equal volume of TNESV buffer and the lysate is clarified by centrifugation at 20,000 g for 20 min. Binding is evaluated by passing the parasite lysate at a flow rate of 1 µL/min in TNESV buffer and measuring the change in refractive index as was done for GA binding in example 3.4.

Compounds thus selected by any of these assays or a combination thereof can then be further tested using known assays described in examples 2.1 and 2.2 and the novel flow cytometry assay as described in example 3.5 to select for the desired anti-malarial effect.

EXAMPLES

Example 1.0

Geldanamycin Binding Site in Pf HSP90

Sequence alignment of Human Hsp90 (α and β) and its homolog Grp94 with PfHsp90 indicates that several domains are evolutionarily conserved suggesting functional similarity among Hsp90 proteins of different organisms. PfHsp90 possesses a charged acidic domain in the central region, which is absent in human Hsp90. N-terminal domain of PfHsp90 shares 69% identity with human Hsp90. Sequence comparison with human Hsp90 reveals that this domain has an ATP/Geldanamycin binding site. The GXXGXG motif in this domain essential for ATP-binding is present in PfHsp90 also. The residues, which make contact with GA in mammalian Hsp90, are also conserved in PfHsp90.

Crystal structure of N-terminal Hsp90-GA complex has already been solved (PDB ID: 1YET) (18). High degree of similarity between the ATP-binding domains of mammalian Hsp90 and PfHsp90 enabled us to model the ATP-binding domain of PfHsp90 using mammalian Hsp90 as a template. N-terminal sequence of PfHsp90 (1-177 amino acids) was submitted to SWISS-MODEL program to obtain the 3-D structure using the crystal structure of N-terminal Human Hsp90 (PDB code: 1YET) as a template. This model was superimposed over the structure of human Hsp90-GA complex using STAMP (Structure Alignment of Multiple Protein) program as shown in FIG. 1a of the accompanying drawings. PfHsp90 is shown in blue line while yellow line denotes mammalian Hsp90. GA is represented in yellow colour in the centre of the structure.

Figure 1B:
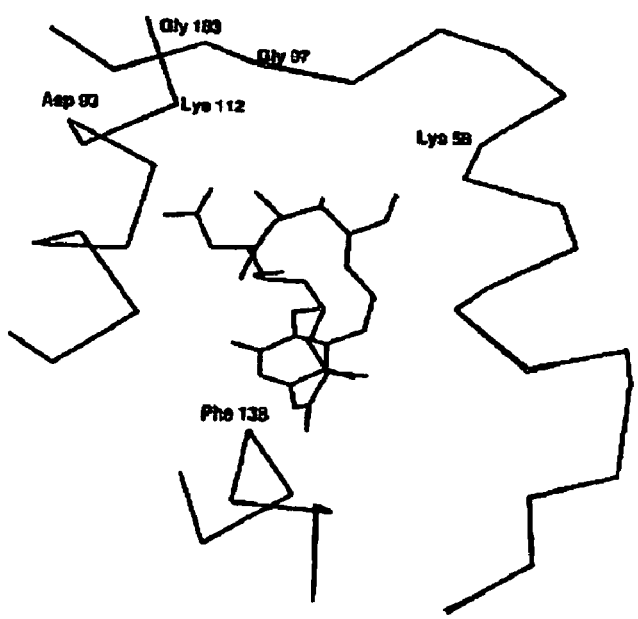

FIG. 1b shows a magnified view of the GA-binding region and the contact making residues, namely Lys 58, Asp 93, Gly 97, Lys 112, Phe 138 and Gly 183 were indicated. Sequence and structure comparison suggests that GA could possibly interact with PfHsp90 also.

Example 2.0

Effect of Ansamycin Antibiotics on Plasmodial Parasite 2.1: Growth Inhibitory Effect of GA:

In order to check if GA could inhibit *Plasmodium falciparum* growth in vitro, we prepared highly synchronous ring-infected parasites using 5% sorbitol. These ring-staged parasites were suspended in RPMI to make 5% hematocrit. 200 µl cell suspension was treated with DMSO or with GA in DMSO at various concentrations (0.5, 1, 5 and 10 µM for 24 h. Smears were taken at the end of treatment, Giemsa-stained and viewed under microscope. While the DMSO treated rings progressed to trophozoite stage at the end of 24 hrs, GA-treated parasites persisted in the ring stage even after 24 hrs. The degree of inhibition in stage progression increased with increasing concentration of GA. Maximal growth inhibition was found at 5 µM concentration. The same experiment was performed with early-trophozoites and schizonts also. When GA was added in the trophozoite stage, 100% growth inhibition was observed at a GA concentration of 10 µM. This correlates with elevated expression of Pfhsp90 in the trophozoite stage compared to ring stage. When schizont-staged parasites were treated with GA, it did not affect the release of merozoites and their subsequent reinvasion of erythrocytes.

2.2: Anti-Malarial Effect of GA and HA

To show the effects of GA on overall parasitemia, ring-infected erythrocytes were either treated with DMSO or with 5 µM GA for 48 hrs (culture was replenished with medium and GA every 24 hrs) and parasitemia was calculated by giemsa staining. While the mock-treated parasites multiplied at the end of 48 hrs, parasitemia was reduced to 50 percent in GA treated cultures by 48 hrs. When cultures were similarly treated with various concentrations of HA (0.5, 1, 5 and 10 µM), maximal reduction in parasitemia was observed at 10 µM concentration.

Examples 2.1 and 2.2 clearly demonstrate that ansamycin antibiotics affect overall parasitemia at the stage of the formation of trophozoites.

Example 3.0

In vitro Assay to Test the Effect of Geldanamycin for Binding to PfHsp90 and Parasite Growth Inhibition 3.1: Solid-Phase GA Binding Assay:

Geldanamycin was immobilized on sepharose beads (9). GA was first modified by adding 1,6-hexanediamine as a linker for coupling to the activated ester beads. 1,6-hexanediamine was added to GA (10 mM in CHCl₃) to yield 10-fold molar excess and allowed to react at room temperature for 2 h in the dark to yield 17-hexamethylenediamine-17-demethoxy-geldanamycin. The reaction solution was extracted with water to remove the unreacted 1,6-hexanediamine. The products were then dried under nitrogen, redissolved in DMSO, and reacted with NHS-activated Sepharose 4 fast flow beads (Amersham Biosciences) for 2 h in the dark at room temperature. The resulting beads were washed twice in ice-cold TNESV buffer (50 mM Tris-HCl, (pH 7.5), 1% NP40, 2 mM EDTA, 100 mM NaCl, 1 mM orthovanadate) and rocked overnight at 4° C. GA beads were then blocked with 1% BSA for 1 h. For control beads, the resin was treated in the same way, but without adding 17-hexamethylenediamine-17-demethoxy-geldanamycin.

3.2: Immunoblot Analysis of PfHSP90 and GA Binding:

*P. falciparum* cultures were treated with saponin at a concentration of 0.075% to release the trophozoites. Saponin released trophozoites of *P. falciparum* were lysed in TNESV buffer (50 mM Tris-HCl, pH 7.5), 1% NP-40, 2 mM EDTA, 100 mM NaCl, 1 mM orthovanadate) containing protease inhibitors. Clarified lysate was incubated with either with GA coupled beads or control beads and incubated overnight at 4° C. Beads were washed four times with TNESV buffer, solubilized in Laemmli buffer and analyzed on SDS-PAGE (7.5% resolving gel with 3% stacker gel) (19). Proteins were transferred to nitrocellulose membrane and the membrane was blocked in 1% milk powder in TBST (20 mM Tris, 136 mM NaCl, 0.05% Tween-20, pH 7.2) for 1 h. The membrane was then washed thrice with TBST for 10 min each. The membrane was then probed with rabbit polyclonal antibody to PfHsp90. After 3 washes with TBST for 10 min each, the membrane was probed with anti-rabbit IgG conjugated to ALP (alkaline phosphatase). The membrane was developed using BCIP (5-bromo, 3-chloro, indolyl phosphate)/NBT (nitroblue tetrazolium) as substrate. Under these conditions, we could clearly see binding of PfHsp90 to the GA-coupled beads. Control beads did not show any binding to PfHsp90.

3.3: Analysis of PfHSP90 and GA Binding by Metabolic Labeling of Proteins:

*P. falciparum* infected erythrocytes in the trophozoite stage were labeled with [$^{35}$S]-cys and [$^{35}$S]-met. Following lysis with 0.075% saponin, parasites were lysed in TNESV buffer containing protease inhibitors. Lysate was incubated with either with GA coupled beads or control beads and tumbled overnight at 4° C. Beads were washed four times with TNESV buffer and solubilized in 2D lysis buffer. The sample in 2D lysis buffer was loaded onto 7 cm×1.5 mm IEF tube gels pre-focused at 250 V for 30 mins. Following this, the tube gels were electrophoresed at 500 V for 4 hours. After the run was over, the tube gels were incubated in 1 ml of equilibration buffer (125 mM Tris (pH 6.8), 4.9 mM DTT, 10% glycerol, and 2% SDS, pH 6.8) for 9 minutes. The tube gels were laid horizontally on top of 7.5% SDS-polyacrylamide gels and sealed with 1% agarose in SDS-PAGE running buffer (50 mM Tris, 380 mM glycine, and 0.1% SDS). SDS-PAGE was carried out at 110V for one hour and 10 minutes. The spots were visualized using fluorography (20). Earlier work from the lab has unequivocally established the position of PfHsp90 (pI=4.94, $M_w$=86 kDa) on 2D-PAGE (21). Based on this, the protein bound to GA coupled beads was identified as PfHsp90. Control beads did not show any binding to PfHsp90.

3.4: Analysis of PfHSP90 and GA Binding by Surface Plasmon Resonance Spectroscopy:

To test the feasibility of a non-radioactive assay for screening GA and related compounds, we used SPR analysis with a BIAcore 2000™ (Amersham Biosciences) biosensor system. Geldanamycin was covalently immobilized on the research CM5 sensor chips at a concentration of 20 mM in 8% DMSO using the amine coupling kit (1-ethyl-3-(dimethylaminopropyl) carbodiimide, N-hydroxysuccinimide) provided by the manufacturer. Nearly 700 resonance units (RU) of GA were immobilized under these conditions. The unreacted moieties on the surface were blocked with 1M ethanolamine. All measurements were carried out with TNESV buffer. The surface was regenerated by a 50-s pulse of 0.5% SDS flowing at 10 µL/min.

For binding analysis, saponin released trophozoites of *P. falciparum* were lysed in an equal volume of TNESV buffer and the lysate was clarified by centrifugation at 20,000 g for 20 min. Binding was evaluated by passing the parasite lysate at a flow rate of 1 µL/min in TNESV buffer and measuring the change in refractive index as response units. Upon passing the parasite lysate over the GA coupled chip, significant binding (response of 900 RU) was observed. In order to make sure that the binding was due to PfHsp90, parasite lysate was mixed with antiserum to PfHsp90 and then passed over the GA coupled chip. In this instance, binding was completely abolished, indicating that PfHsp90 from the Parasite lysate was specifically binding to GA coupled in the chip.

3.5: Analysis of the Inhibition of *P. falciparum* Growth by GA Using Flow Cytometry In order to confirm *P. falciparum* inhibition by GA and related compounds, we developed an assay involving flow cytometry. Briefly, parasites were purified on 75% percoll thrice in order to obtained a pure parasite population free of uninfected RBCs. 30 µL of such a suspension was added to 600 µL of the staining solution (6 mg/L of acridine orange in 10 mM Tricine and 120 mM $NaH_2PO_4$ at pH 9). The suspension of stained cells was injected into a flow cytometer (BD (Becton Dickinson) FACScan) equipped with an argon ion laser set at 488 nm at a power output of 15 mW. Green fluorescence (GF) was detected at 560 nm. Side scatter (SSC) was detected simultaneously with GF. At most, 10,000 cells were assessed and plotted in a two-dimensional scattergram of SSC (linear scale) against GF (logarithmic scale) in less than 60 seconds. The parasite area was defined in a two dimensional scattergram of SSC vs. GF. The ring and trophozoite forms were clearly defined by analysis of scattergrams for parasites at various times after synchronization. The validity of the assay was confirmed by treating highly synchronous ring stage parasites with 10 µM GA for 24 h. DMSO treated parasites were used as control. GA treated parasites displayed a scattergram corresponding to rings while the scattergram of the DMSO treated control corresponded to that of trophozoites. The data clearly demonstrates that GA and related compounds can be effective as anti-malarials.

Based on the assays described in example 3 of this specification, it is feasible for one skilled in the art to develop similar assays and to test for the binding of test compounds to Pfhsp90 (using solid phase coupling to sepharose beads and BIACORE chips) as well as for inhibition of the growth of *P. falciparum* (using the flow cytometry assay).

REFERENCES

1. Borkovich K. A., Farrelly F. W., Finkelstein D. B., Taulien J. and Lindquist S. (1989) Hsp82 is an essential protein that is required in higher concentrations for growth of cells at higher temperature. *Mol. Cell Biol.* 9, 3919-3930.
2. Rutherford S. L. and Lindquist S. (1998) Hsp90 as a capacitor for morphological evolution. *Nature* 396, 336-342.

3. Queitsch C., Sangster T. A. and Lindquist S. (2002) Hsp90 as a capacitor for phenotypic variation. *Nature* 417, 618-624.
4. Csermely P., Schnaider T., Soti C., Prohaszka Z. and Nardai G. (1998) The 90-kDa molecular chaperone family: structure, function, and clinical applications. A comprehensive review. *Pharmacol. Ther.* 79, 129-168.
5. Buchberger A. and Bakau B. (1997) *Guidebook to Molecular Chaperones and protein-folding catalysts*. Oxford University Press, Oxford, UK, pp. 147.
6. Murphy P. J. M., Kanelakis K. C., Galigniana M. D., Morishima Y and Pratt W. B. (2001) Stoichiometry, abundance and functional significance of the hsp90/hsp70-based multiprotein chaperone machinery in reticulocyte lysate. *J. Biol. Chem.* 276, 30092-30098.
7. Blagosklonny M V. (2002) Hsp90-associated oncoproteins: multiple targets of geldanamycin and its analogs. Leukemia 16, 455-462.
8. Grenert J. P., Sullivan W. P., Fadden P., Haystead T. A. J., Clark J., Mimnaugh E., Krutzsch H., Ochel H. J., Schulte T. W., Sausville E., Neckers L. M. and Toft D. O. (1997) The Amino-terminal domain of heat shock protein 90 (hsp90) that binds geldanamycin is an ATP/ADP switch domain that regulates hsp90 conformation. *J. Biol. Chem.* 272, 23843-23850.
9. Whitesell L., Mimnaugh E. G., Costa B., Myers C. E. and Neckers L. M. (1994) Inhibition of heat shock protein Hsp90-pp60 v-src heteroprotein complex formation by benzaquinone ansamycins: Essential role for stress proteins in oncogenic transformation. *Proc. Natl. Acad. Sci. USA* 91, 8324-8328.
10. Schneider C., Lorenzino L., Nimmesgem E., Ouerfelli O., Danishefsky S., Rosen N. and Hartl U. F. (1996) Pharmacologic shifting of a balance between protein refolding and degradation mediated by Hsp90. *Proc. Natl. Acad. Sci. USA* 93, 14536-14541.
11. Bannister L. H., Hopkins J. M., Fowler R. E., Krishna S. and Mitchell G. H. (2000) A brief illustrated guide to the ultrastructure of *Plasmodium falciparum* asexual blood stages. *Parasitology Today* 6,427433.
12. Das A., Syin C., Fujioka H., Zheng H., Goldman N., Aikawa M. and Kumar N. (1997) Molecular characterization and ultrastructural localization of *Plasmodium falciparum* Hsp60. *Mol. Biochem Parasitol.* 88, 95-104.
13. Kumar N., Koski G., Harada M., Aikawa M. and Zheng H. (1991) Induction and localization of *Plasmodium falciparum* stress proteins related to the heat shock protein 70 family. *Mol. Biochem. Parasitol.* 48, 47-58.
14. Jendoubi M., Dubois P. and Silva L. P. (1985) Characterization of one polypeptide antigen potentially related to protective immunity against the blood infection by *Plasmodium falciparum* in the squirrel monkey. *J. Immunol.* 134,1941-1945.
15. Bonnefoy S., Attal G., Langsley G., Tekaia F. and Puijalon O. M. (1994) Molecular characterization of the heat shock protein 90 gene of the human malarial parasite *Plasmodium falciparum*. *Mol. Biochem. Parasitol.* 67,157-170.
16. Banumathy G, Singh V, Pavithra S R, Tatu U. (2003) Heat shock protein 90 function is essential for *Plasmodium falciparum* growth in human erythrocytes. *J. Biol. Chem.* 278, 18336-45.
17. Kumar R, Musiyenko A, Barik S. (2003) The heat shock protein 90 of *Plasmodium falciparum* and anti-malarial activity of its inhibitor, geldanamycin. *Malar J.* 2, 30-41.
18. Stebbins C. E., Russo A. A., Schneider C., Rosen N., Hartl F. U. and Pavletich N. P. (1997) Crystal structure of an Hsp90-geldanamycin complex: Targeting of a protein chaperone by an antitumor agent. *Cell* 89, 239-250.
19. Laemmli U. K. (1970) Cleavage of structural proteins during the assembly of the head of bacteriophage T4. *Nature* 227, 680-685.
20. O'Farrell P. H. (1975) High resolution two dimensional gel electrophoresis of proteins. J. Biol. Chem. 250, 4007-4021.
21. Banumathy G, Singh V, Tatu U. (2002) Host chaperones are recruited in membrane-bound complexes by *Plasmodium falciparum*. *J. Biol. Chem.* 277, 3902-12.
22. McInnes J. (1990) Preparation and uses of photobiotin. *Meth. Enzymol.* 184, 588-600.

The invention claimed is:

1. An assay to screen anti-malarial drugs by testing for binding of a test compound with plasmodium 90 kDa heat shock protein which comprises:
    (a) immobilizing said test compound covalently on a matrix thereby forming an immobilized test compound;
    (b) reacting saponin-freed Plasmodial trophozoite lysate comprising plasmodium 90 kDa heat shock protein with said immobilized test compound;
    (c) detecting binding of plasmodium 90 kDa heat shock protein to said immobilized test compound;
    (d) selecting said test compound if binding between said plasmodium 90 kDa heat shock protein and said immobilized test compound is detected in step (c);
    (e) measuring growth of *Plasmodium falciparum* in an assay comprising measuring the number of *P. falciparum* ring forms growing into *P. falciparum* trophozoite forms with and without said selected test compound, said number of ring forms and said trophozoite forms being measured with flow cytometry;
    (f) comparing the growth of *P. falciparum* in said growth assay with and without said selected test compound; and
    (g) detecting a decrease in said measured growth of *P. falciparum* exposed to said selected test compound as compared to the growth of *P. falciparum* not exposed to said selected test compound as being indicative of said selected test compound being an anti-malarial drug.

2. The assay as claimed in claim 1, wherein the plasmodium 90 kDa heat shock protein is from *Plasmodium falciparum*.

3. The assay as claimed in claim 1, wherein said matrix is selected from the group consisting of agarose and carboxymethylated dextran.

4. The assay as claimed in claim 3, wherein said carboxymethylated dextran matrix is attached to a gold surface.

5. The assay as claimed in claim 1, wherein detecting binding of plasmodium 90 kDa heat shock protein to said immobilized test compound comprises detecting plasmodium 90 kDa heat shock protein with immunochemical methods, radiochemical methods or non-radioactive methods.

6. The assay as claimed in claim 5, wherein said radiochemical methods are selected from a group comprising 2D gel electrophoresis or fluorography.

7. The assay as claimed in claim 1, wherein said test compound is derivatized with an amine functional group, and said matrix comprises a plurality of carboxylate functional groups.

8. An assay to screen anti-malarial drugs by testing for binding of a test compound with plasmodium 90 kDa heat shock protein which comprises:
    (a) derivatizing a test compound with an amine functional group;
    (b) immobilizing said derivatized test compound on a surface of a carboxymethylated dextran matrix having a plurality of carboxylate groups thereby forming an immobilized test compound, said immobilizing comprises admixing said derivatized test compound at a concentration of 20 mM in 8% dimethyl sulfoxide (DMSO) with 1-ethyl-3-(dimethylaminopropyl) carbodiimide hydrochloride, N-hydroxysuccinimide and ethanolamine HCl and said surface of said carboxymethylated dextran matrix forming an amide bond between said derivatized test compound amine groups and said carboxymethylated dextran matrix carboxylate groups;

(c) blocking said carboxylate groups on said carboxymethylated dextran matrix not forming said amide bond with said immobilized test compound comprising adding 1M ethanolamine to said carboxylated dextran matrix after addition of said derivatized test compound;

(d) regenerating said matrix surface by a 50 s pulse of 0.5% SDS flowing at 10 µL/min;

(e) preparing a saponin-freed Plasmodial trophozoite lysate comprising mixing one volume of saponin-freed Plasmodial trophozoites and one volume of Tris-HCl buffer containing nonyiphenoxy polyethoxy ethanol (TNESV buffer);

(f) clarifying said lysate by centrifuging said saponin-freed Plasmodial trophozoite lysate at 20,000 g for 20 min;

(g) reacting said immobilized test compound with said clarified saponin-freed Plasmodial trophozoite lysate by passing said saponin-freed Plasmodial trophozoite lysate at a flow rate of 1 µL/min in TNESV buffer over said immobilized test compound on said matrix and measuring a change in refractive index as response units;

(h) washing said carboxymethylated dextran matrix to remove unbound plasmodium 90 kDa heat shock protein;

(i) detecting binding of a plasmodium 90 kDa heat shock protein to said immobilized test compound;

(j) selecting said test compound if binding between said plasmodium 90 kDa heat shock protein and said immobilized test compound is detected in step i;

(k) measuring growth of *Plasmodium falciparum* in an assay comprising measuring the number of *P. falciparum* ring forms growing into *P. falciparum* trophozoite forms with and without said selected test compound free of said matrix, said number of ring forms and said trophozoite forms being measured with flow cytometry;

(l) comparing the growth of *P. falciparum* in said growth assay with and without said selected test compound; and (m) detecting a decrease in said measured growth of *P. falciparum* exposed to said selected test compound as compared to the growth of *P. falciparum* not exposed to said selected test compound as being indicative of said selected test compound being an anti-malarial drug.

9. The assay as claimed in claim 8, wherein detecting binding of plasmodium 90 kDa heat shock protein to said immobilized test compound comprises detecting plasmodium 90 kDa heat shock protein with immunochemical methods, radiochemical methods or non-radioactive methods.

* * * * *

UNITED STATES PATENT AND TRADEMARK OFFICE
CERTIFICATE OF CORRECTION

PATENT NO. : 7,611,853 B2  Page 1 of 1
APPLICATION NO. : 10/539728
DATED : November 3, 2009
INVENTOR(S) : Utpal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 825 days.

Signed and Sealed this

Twelfth Day of October, 2010

David J. Kappos
*Director of the United States Patent and Trademark Office*